US012016779B2

(12) United States Patent
Lieberman et al.

(10) Patent No.: US 12,016,779 B2
(45) Date of Patent: *Jun. 25, 2024

(54) GROWTH FACTOR TRANSDUCED CELL-LOADED CERAMIC SCAFFOLD FOR BONE REGENERATION AND REPAIR

(71) Applicant: UNIVERSITY OF SOUTHERN CALIFORNIA, Los Angeles, CA (US)

(72) Inventors: Jay R. Lieberman, Los Angeles, CA (US); William Pannell, Los Angeles, CA (US); Yong Chen, Los Angeles, CA (US); Xuan Song, Los Angeles, CA (US); Sofia Bougioukli, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 1237 days.

This patent is subject to a terminal disclaimer.

(21) Appl. No.: 16/337,893

(22) PCT Filed: Sep. 29, 2017

(86) PCT No.: PCT/US2017/054609
§ 371 (c)(1),
(2) Date: Mar. 28, 2019

(87) PCT Pub. No.: WO2018/064631
PCT Pub. Date: Apr. 5, 2018

(65) Prior Publication Data
US 2020/0022816 A1 Jan. 23, 2020

Related U.S. Application Data

(60) Provisional application No. 62/401,745, filed on Sep. 29, 2016.

(51) Int. Cl.
*A61F 2/30* (2006.01)
*A61F 2/28* (2006.01)
(Continued)

(52) U.S. Cl.
CPC ............ *A61F 2/30942* (2013.01); *A61F 2/28* (2013.01); *A61K 38/1875* (2013.01);
(Continued)

(58) Field of Classification Search
None
See application file for complete search history.

(56) References Cited

U.S. PATENT DOCUMENTS 6,077,987 A 6/2000 Breitbart et al.
6,730,252 B1 * 5/2004 Teoh ...................... A61L 27/18
264/234
(Continued)

OTHER PUBLICATIONS

Trombetta et al. "3D Printing of Calcium Phosphate Ceramics for Bone Tissue Engineering and Drug Delivery" Annals of Biomedical Engineering, Jun. 2016, 45(1), 23-44. (Year: 2016).*
(Continued)

*Primary Examiner* — Carlos A Azpuru
*Assistant Examiner* — Casey S Hagopian
(74) *Attorney, Agent, or Firm* — SNELL & WILMER LLP

(57) ABSTRACT

A method for repairing a bone defect of a patient includes providing a ceramic scaffold configured for filling the bone defect, loading the scaffold with growth factor transduced cells incorporating a gene that encodes a growth factor essential for bone formation, placing the ceramic scaffold with the growth factor transduced cells in or across the bone defect, and stabilizing the ceramic scaffold with the growth factor transduced cells in the patient until the bone defect is healed. An assembly for repairing a bone defect includes a (Continued)

ceramic scaffold configured for spanning the bone defect and a culture of live growth factor transduced cells incorporating a gene that encodes a growth factor essential for bone formation loaded onto the ceramic scaffold.

6 Claims, 6 Drawing Sheets

(51) Int. Cl.
    *A61K 38/18*     (2006.01)
    *A61L 27/10*     (2006.01)
    *A61L 27/38*     (2006.01)
    *A61L 27/54*     (2006.01)
    *B33Y 10/00*     (2015.01)
    *B33Y 80/00*     (2015.01)

(52) U.S. Cl.
    CPC ............ *A61L 27/10* (2013.01); *A61L 27/3834* (2013.01); *A61L 27/54* (2013.01); *A61F 2002/30235* (2013.01); *A61F 2002/30677* (2013.01); *A61F 2002/30784* (2013.01); *A61F 2310/00293* (2013.01); *A61L 2300/414* (2013.01); *A61L 2430/02* (2013.01); *B33Y 10/00* (2014.12); *B33Y 80/00* (2014.12)

(56) References Cited

U.S. PATENT DOCUMENTS

| | | | |
|---|---|---|---|
| 2004/0078090 A1 | 4/2004 | Binette et al. | |
| 2014/0178346 A1* | 6/2014 | Byrne ................ | A61K 38/1875 424/93.21 |
| 2020/0316258 A1 | 10/2020 | Lieberman et al. | |

OTHER PUBLICATIONS

International Preliminary Report on Patentability dated Apr. 2, 2019 in Application No. PCT/US2017/054609.

International Search Report and Written Opinion of the International Searching Authority (dated Dec. 14, 2017) for Corresponding International PCT Patent Application No. PCT/US17054609, filed Sep. 29, 2017.

Trombetta et al. "3D Printing of Calcium Phosphate Ceramics for Bone Tissue Engineering and Drug Delivery" Annals of Biomedical Engineering, vol 45 Issue 1 (Jun. 20, 2016); pp. 23-44; entire document, but especially: abstract, p. 24 col. 1 para 1, p. 24 col. 1 para 2, p. 24 col. 2 para 1, fig 1(a).

Li et al. "Macroporous Biphasic Calcium Phosphate Scaffold with High-Permeability/Prosity Ratio" Tissue Engineering, vol. 9 Issue 3 (Jul. 9, 2004): pp. 535-548; entire document.

Wilson et al. "Design and fabrication of standardized hydroxyapatite scaffolds with a defined macro-architecture by rapid prototyping for bone-tissue-engineering research" Journal of Biomedical Materials Research, vol. 68A Issue 1 (Jan. 1, 2004); pp. 123-132; entire document.

Bougioukli et al. "In vitro evaluation of a lentiviral two-step transcriptional amplification system using GAL4FF transactivator for gene therapy applications in bone repair", Gene Therapy; 25:260-268 (2018).

* cited by examiner

Cell viability after 72 hours of culture on 3D printed disk in vitro.

Microscopic image at 2.5x magnification of cell viability on 3d-printed disc after 72 hours of culture in vitro. Gray signal represents live cells and isolated black circles represent areas of dead cells. White or light gray represents no signal.

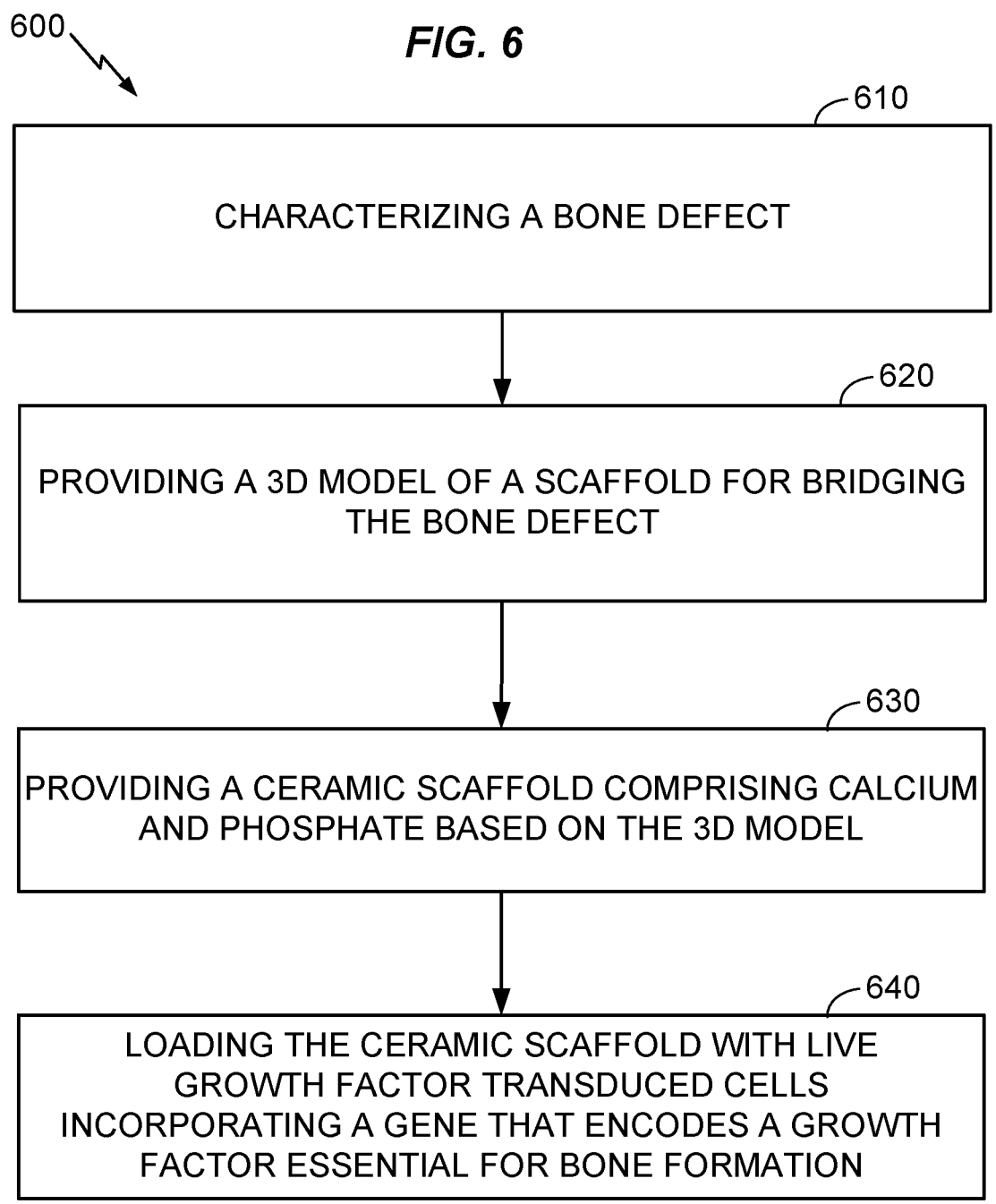

GROWTH FACTOR TRANSDUCED CELL-LOADED CERAMIC SCAFFOLD FOR BONE REGENERATION AND REPAIR

CROSS-REFERENCE TO RELATED APPLICATION

This application claims the benefit and priority of U.S. provisional patent application Ser. No. 62/401,745 filed Sep. 29, 2016, which is incorporated herein in its entirety by reference.

GOVERNMENT LICENSE RIGHTS

This invention was made with government support under contract number R01 AR057076 awarded by the National Institutes of Health, and contract No. 1335476 awarded by the National Science Foundation. The government has certain rights in the invention.

FIELD

The present disclosure relates to methods and apparatus for repairing bone tissue, and more particularly to combined use of custom 3D-printed calcium phosphate scaffolds and regional gene therapy in bone graft scenarios to heal critical sized bone defects.

BACKGROUND

Fracture non-union and inadequate bone formation in settings such as trauma, tumor, joint replacement and limb reconstructive surgeries are among the most challenging problems in orthopedic surgery. Autologous bone graft is the gold standard to use in such situations, but its disadvantage is limited availability of the graft and complications and pain associated with graft harvest. Researchers have explored the option of using precursor cells (from bone marrow, fat, muscle or other tissues) that have potential to transform into bone forming cells, but the methods to purify these cells and potential of these cells to form bone are limited unless stimulated by the growth factors. Regional gene therapy is an attractive option as it potentially allows the investigator to incorporate the desired gene encoding the growth factor essential for bone formation into the host cells and implant these cells back into the host at a particular site where they induce new bone formation.

Prior research has reported on the effect of regional gene therapy with bone morphogenetic protein-2-producing bone marrow cells on the repair of bone defects in rats, showing promise as one aspect of bone replacement therapy. "3D printing" broadly understood as additive manufacturing, has been proposed for forming scaffolds of calcium phosphate and collagen for bone regeneration, but not in conjunction with regional gene therapy. Additive manufacturing provides the advantage of custom shaping for individual bone replacement therapy, but its suitability in conjunction with regional gene therapy is poorly understood, if at all.

Bone regeneration in vivo or in vitro is desirable for providing more rapid and more effective clinical outcomes for treatment of severe bone injury. It would be desirable, therefore, to provide more effective methods and apparatus for bone regeneration and replacement of lost bone tissue.

SUMMARY

This summary and the following detailed description should be interpreted as complementary parts of an integrated disclosure, which parts may include redundant subject matter and/or supplemental subject matter.

A method for repairing a bone defect of a patient may include providing a ceramic scaffold configured for spanning the bone defect. The method may further include loading the scaffold with one or more growth factor transduced cell lines (e.g., mesenchymal stem cells) incorporating a gene that encodes a growth factor essential for bone formation. A cell line altered to incorporate a gene that encodes a growth factor essential for bone formation is referred to herein as a "growth factor transduced" cell line. The method may further include placing the ceramic scaffold with the growth factor transduced cells in or across the bone defect. The method may further include stabilizing the ceramic scaffold with the growth factor transduced cells in the patient until the bone defect is healed, using any suitable stabilizing technique.

In a related aspect, an assembly for repairing a bone defect may include a ceramic scaffold configured for spanning the bone defect and a culture of live growth factor transduced cells incorporating a gene that encodes a growth factor essential for bone formation loaded onto the ceramic scaffold. The ceramic scaffold may be, or may include, a calcium phosphate material. In an aspect, the ceramic scaffold may include a 3D printed calcium phosphate material. The ceramic scaffold may shaped to match the bone in the areas adjacent to the defect, so as to fit closely to the bone while spanning the defect.

To the accomplishment of the foregoing and related ends, one or more examples comprise the features hereinafter particularly pointed out in the claims and fully described in the detailed description after the drawings.

BRIEF DESCRIPTION OF THE DRAWINGS

FIG. 6 is a flow chart illustrating operations and aspects of making a ceramic scaffold with the growth factor transduced cells.

DETAILED DESCRIPTION

The present disclosure concerns use of regional gene therapy with transduced growth factor transduced cells in bone graft scenarios with 3D-printed scaffolds. The combination of these technologies represents an innovative method of grafting bone with many potential clinical applications. The disclosure below describes experiments and experimental results achieved by the inventors, followed by a summary of the novel subject matter underlying the experiments.

3D Printing

Calcium phosphate (CaP) scaffolds were 3D printed using a slurry-based stereolithography process as developed by Dr. Song Chen et al. in *Ceramic Fabrication Using Mask-Image-Projection-based Stereolithography Integrated with*

Tape-casting. *Journal of Manufacturing Processes*, 2015; 20(3):456-464. Briefly, this 3D printing technique is performed by first mixing a ceramic powder (CaP) with a photopolymer resin to create a slurry. A tape casting system is used to aid the recoating of each slurry layer. A light source then activates the resin, curing it layer by layer until an object is built. The object, which is still a mixture of ceramic and resin, is then heated in a furnace to burn out the resin. Since the resin has a much lower melting temperature than the ceramic, the ceramic part of interest is left behind as the final product.

Figure 5:
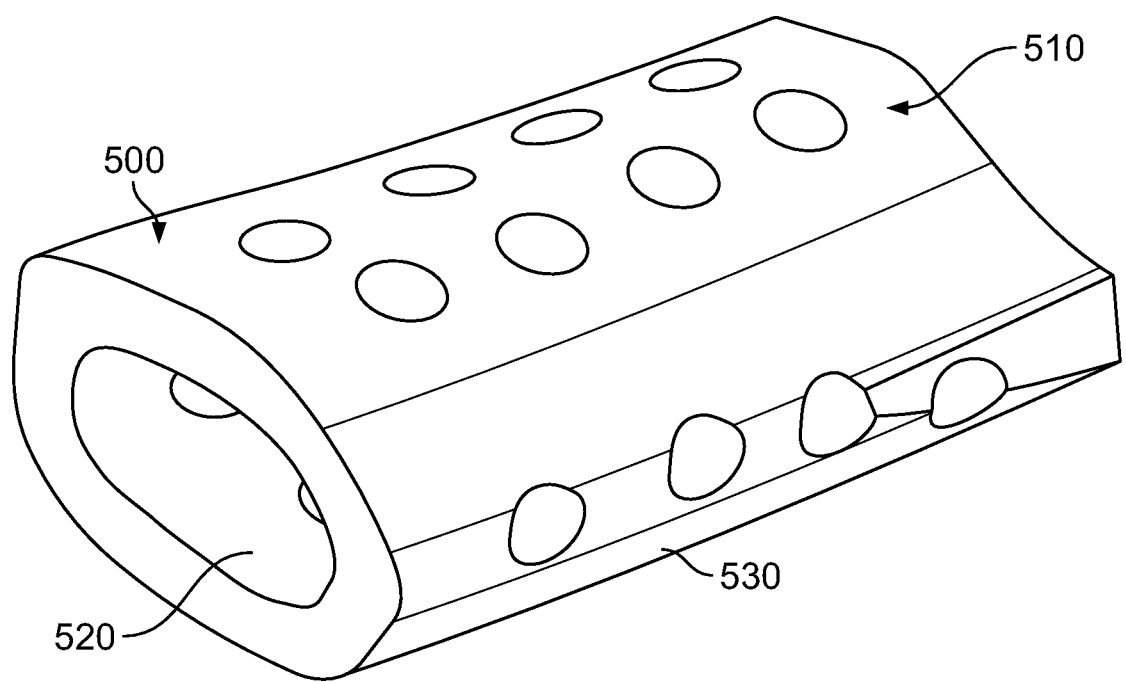
FIG. 5 is a perspective view showing an example of a 3D printed ceramic scaffold for bone repair.

In our experiments, Computer Aided Software (CAD) was first used to create a hollow elliptical cylinder 6 mm in length in order to approximate the size and shape of a rat critical sized femoral defect. These scaffolds were 3D printed using commercially available calcium phosphate powder (Alfa Aesar #89836). An example of a resulting scaffold 500 is shown in FIG. 5.

Regional Gene Therapy

Virk et al. 2011 ("Same day" ex-vivo regional gene therapy: a novel strategy to enhance for bone repair. *Mol Ther.* 2011; 19:960-968) describes the gene therapy in detail. Briefly, a lentiviral based system (LV-BMP2) was created expressing bone morphogenetic protein 2 (BMP-2). Cultured rat bone marrow cells were transduced using a multiplicity of infection (MOI) of 25. These cells were used in the experiments detailed below.

Dr. J. R. Lieberman's and associates have focused on the development of regional gene therapy to treat large-scale bone loss using a rodent model. His lab has demonstrated that a critical sized defect (the size at which the bone will not heal on its own) created in a rodent femur can heal with the application of lentiviral transduced rat bone marrow cells (RBMC) by loading them on a commercially available carrier (collagen sponge or compression resistant matrix) and placing the carrier in the defect (Virk et al. 2011).

Our experiments evaluated custom 3D-printed scaffolds combination with genetically modified cells as disclosed in Virk et al, 2011.

Results

In Vitro BMP-2 Production

BMP-2 production of transduced RBMC was tested in vitro after 48 hours and 14 days of cell culture on 15 mm diameter, 2 mm thick 3D printed discs. At 48 hours BMP-2 production was higher on 3D-printed scaffolds as compared to control (Table 1).

TABLE 1

| ng BMP-2 production per 10,000 cells | | |
|---|---|---|
| | 48 Hours | 14 Days |
| Non-transduced RBMC | 0.00 | 0.03 |
| LV-BMP2 + 3D disc | 1.71 | 48.62 |
| LV-BMP2 | 1.26 | 157.35 |

Based on our work, in vitro BMP-2 production on the 3D printed discs is sufficient to heal a critically sized rat femoral defect.

In Vitro Cell Viability

Figure 1:
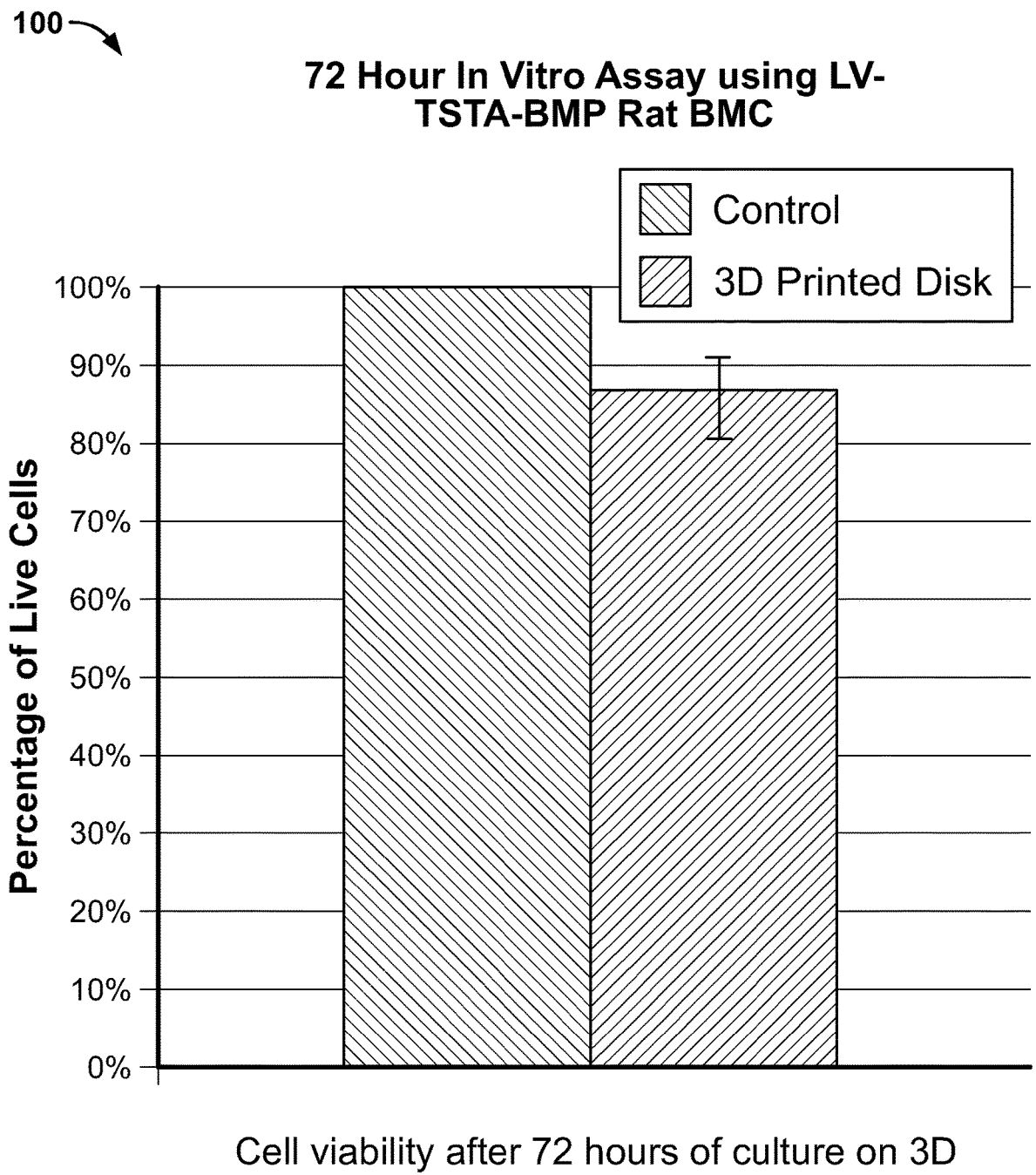
FIG. 1 is a chart showing in vitro results of a trial using gene therapy in conjunction with a 3D printed ceramic scaffold.
Figure 2:
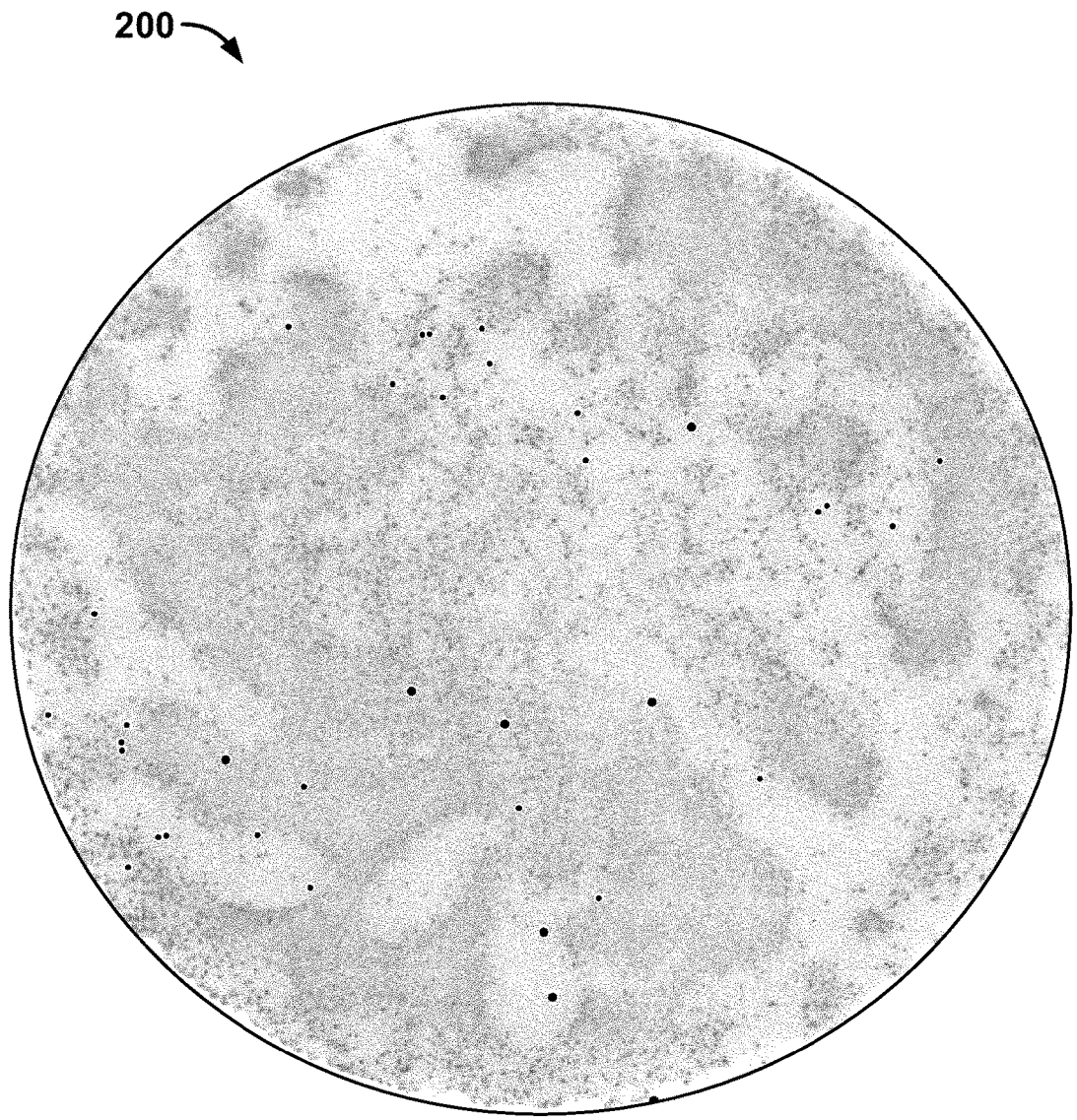
FIG. 2 is a grayscale rendering of a photo illustrating cell viability of transduced cells on a 3D printed ceramic scaffold disk after 72 hours.

Transduced rat bone marrow cells (RBMC) were cultured in vitro on top of 3D printed CaP discs for 72 hours. Cell viability was determined using a commercially available Live/Dead assay kit (BioVision K501). Cells cultured on CaP disks demonstrated excellent viability at 72 hours compared to a control (standard culture well). Cell viability on 3d printed discs averaged 85% (SD 6%) relative to the control (FIG. 1 at graph 100, FIG. 2 at photo 200). These cell viability results are higher than a published study using comparable 3D printed calcium phosphate/collagen combination scaffolds (Inzana J, Olvera D, Fuller S, et al. *3D printing of composite calcium phosphate and collagen scaffolds for bone regeneration. Biomaterials.* 2014; 35:4026-4034).

In Vivo Bone Formation

Figure 3:
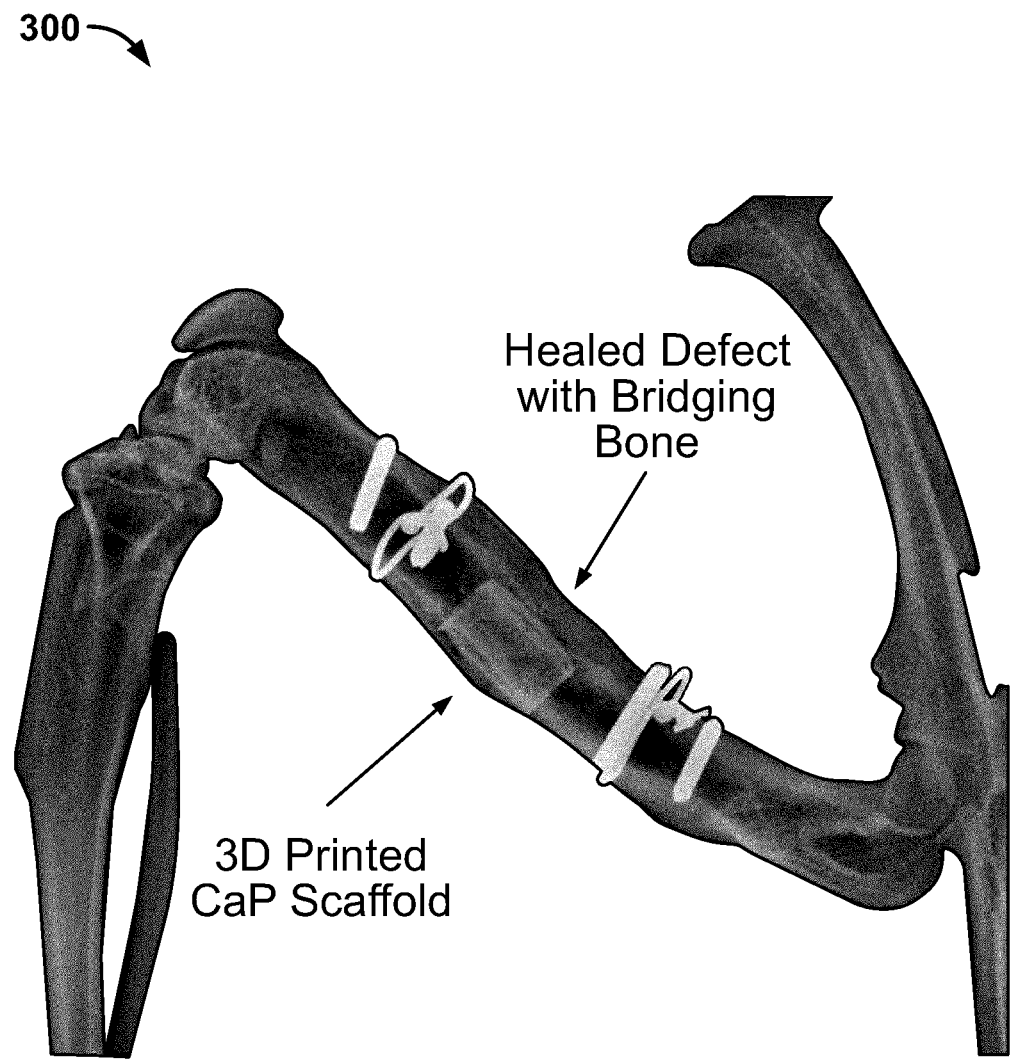
FIG. 3 is an X-ray image showing results of a successful rat bone repair using a method as disclosed herein.

A pilot experiment using a 12-week-old Lewis rat was performed. A standard 6-mm mid-diaphyseal femoral defect was created as described in prior publications (Alae, F., Liebermen, J. R., et al., Biodistribution of LV-TSTA transduced rat bone marrow cells used for "ex-vivo" regional gene therapy for bone repair. *Curr Gene Ther.* 2015; 15(5): 481-491, and Virk et al. 2011). A 3D printed CaP scaffold loaded with 5 million lentiviral transduced rat bone marrow cells was placed in the defect. The defect was healed 8 weeks after the surgical procedure (FIG. 3 at x-ray image 300). The 3D printed CaP scaffold 310 itself and the regenerated "bridging bone" 320 are clearly visible and pointed out in FIG. 3. A drawing of a model for a similar 3D printed CaP scaffold 500 is shown in FIG. 5. FIG. 2 shows a culture 200 of mesenchymal stem cells incorporating a gene that encodes a growth factor essential for bone formation, grown on a CaP ceramic disk.

Scaffold Shaping and Configuration; Results

More recently, Computed Tomography (CT) data from an intact rodent femur was obtained from our labs prior work. Commercially available software (Mimics; Materialise NV, Leuven, Belgium) was then used to convert a 6 mm section of diaphyseal bone into a file type compatible with 3D printing software, resulting in a model of a scaffold 500 as shown in FIG. 5. Additionally, 700-micrometer holes 510 were added to the model scaffold to facilitate cellular growth and communication.

An alternative ceramic powder, beta Tri-Calcium Phosphate (beta TCP), may also be used to 3D print the scaffolds. We have 3D printed scaffolds based on the "rodent specific" CT data. These may be tested following similar methods as described above.

Prior to surgical implantation, the scaffold and loaded cells form an assembly made of a ceramic scaffold 500 configured for spanning the bone defect, and a culture of live mesenchymal stem cells 200 or other growth factor transduced cells incorporating a gene that encodes a growth factor essential for bone formation loaded onto the ceramic scaffold. Suitable cells for being transduced with one or more genes that encode a growth factor may include, for example, mesenchymal cells, bone marrow cells, fibroblasts, adipose-derived cells, umbilical cord cells, or muscle cells. The ceramic material may include, for example, CaP or beta TCP. In a clinical setting, the assembly may be prepared in advance of surgery and maintained alive in vitro until surgical implantation. In an alternative, the surgeon may load live growth factor transduced cells on the ceramic scaffold for the first time after it is in place in the patient's body (in vivo), or may supplement an in vitro loading of cells with a second application in vivo.

The scaffold may be thinner than the bone wall to be repaired and perforated with circular openings 510 in the range of about 300 to 1000 microns, for example, about 500 to 700 microns, or about 700 microns. The openings 510 may be spaced as desired to facilitate bone regrowth, for example, uniformly or semi-uniformly center-to-center spaced at about 1.5 to 5 times the opening's largest diameter.

The scaffold is generally tube-shaped with an interior surface 520 and exterior surface 530. The assembly of scaffold and live growth factor transduced cells enables regeneration of structural bone tissue from the loaded cell culture on its openings 510, exterior 530, interior 520 and by recruitment of local progenitor cells.

Flowcharts and Methods

Figure 4:
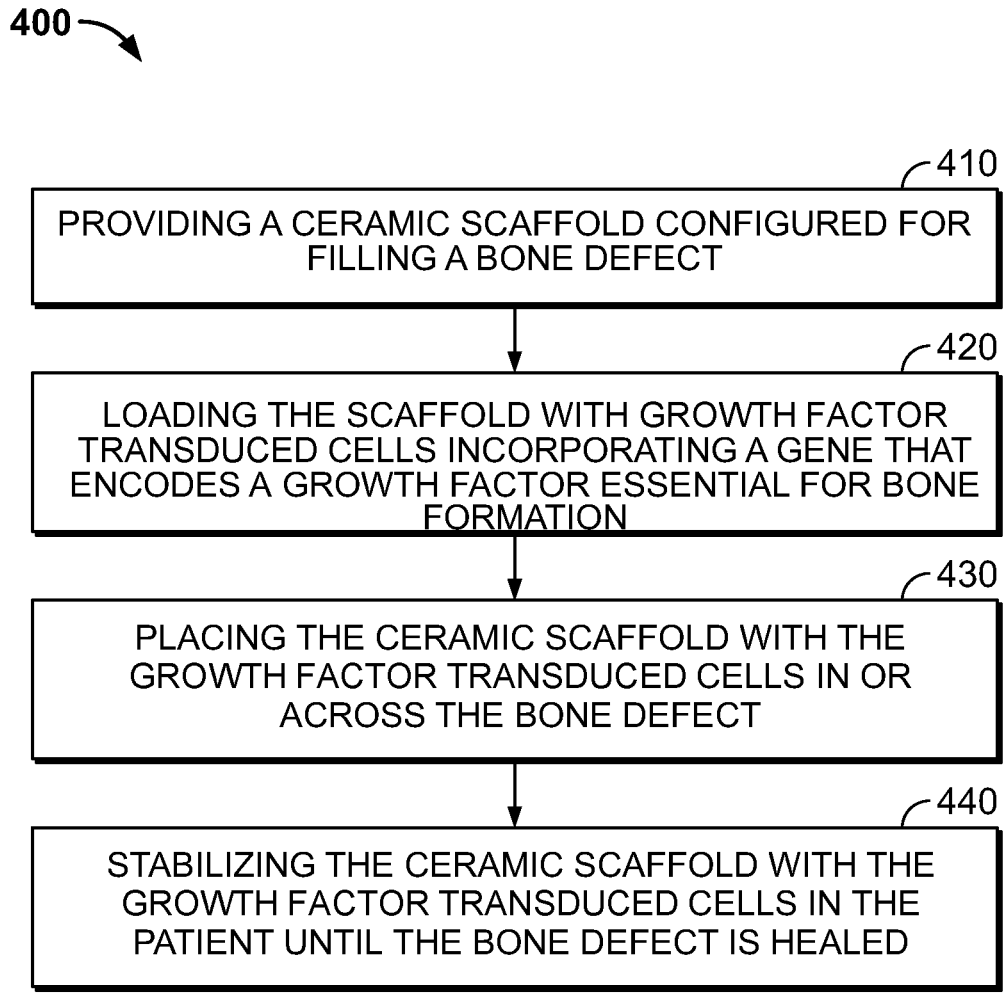
FIG. 4 is a flowchart illustrating operations and aspects of a method for repair of a bone defect.

Referring to FIG. 4, a method 400 for repairing a bone defect of a patient may include, at 410, providing a ceramic scaffold configured for spanning the bone defect, for example, by 3D printing a CaP or other ceramic scaffold or by obtaining a pre-printed scaffold from a manufacturer sized to span the bone defect, for example based on a preceding CT scan as for the rodent femur described above. The method 400 may further include, at 420, loading the scaffold with growth factor transduced cells incorporating a gene that encodes a growth factor essential for bone formation, for example, by preparing or obtaining a culture of lentiviral transduced bone marrow cells as described herein, applying the culture to the scaffold, and confirming viability of the culture loaded on the scaffold prior to implantation. For example, the scaffold with pre-loaded mesenchymal cells as described may be obtained in the form of a prepared assembly from an independent source, e.g., a specialized laboratory, or the cell preparation and loading of the scaffold may be performed by a laboratory controlled by the facility performing the scaffold-implantation surgery. The method may further include, at 430, placing the ceramic scaffold with the growth factor transduced cells in or across the bone defect.

The method 400 may further include, at 440, stabilizing the ceramic scaffold with the growth factor transduced cells in the patient until the bone defect is healed, using any suitable stabilizing technique. The ceramic scaffold is semi-structural and designed for load sharing. The scaffold may not be strong enough by itself to stabilize the defect without load sharing from other structural members. Depending on the nature of the defect, it may be stabilized using biocompatible metal plates, rods, or other suitable structural members.

The enumerated operations 410, 420, 430, 440 may be performed in any operable order with suitable modifications. For example, the operation 430 placing the ceramic scaffold in or across the defect may be performed, but without first loading growth factor transduced cells onto the ceramic. Then, the operation 420 of loading the scaffold with growth factor transduced cells may be performed while the scaffold is in place around the defect. For example, the growth factor transduced cells may be suspended in a bio-compatible fluid and applied to the ceramic scaffold in vivo or in vitro, using a pipette or other suitable fluid applicator.

Referring to FIGS. 5 and 6, further aspects of the present disclosure may include a method 600 for making a ceramic scaffold 500 loaded with growth factor transduced cells as described herein, for use in the method 400 or other suitable method. The method 600 may include, at 610, characterizing a specific bone defect of a patient. For example, the operation 610 may include scanning a bone defect by a 3D scanner, for example, a CT scanner, digitizing 3D information obtained by the scanning, and associating the digitized information with an identifier for the patient and defect site. In an alternative, the characterizing 610 may include receiving information that associates an identifier for a patient and/or bone defect with 3D information relating to the defect or to a scaffold for bridging the defect.

Further aspects of the method 600 may include, at 620, providing a 3D model of a scaffold for bridging the bone defect characterized by the first operation 610. As used herein, "providing" includes but is not limited to engaging a person or entity to create the 3D model based on the data characterizing the bone defect. For example, a medical technician may design a 3D model to fit stable portions of the bone that are expected to remain as scanned after the bone defect is prepared for repair, e.g., by cleaning out damaged tissue. The stable regions of the bone may be adjacent to defective regions of the bone.

The method 600 may further include, at 630, providing a ceramic scaffold that includes calcium and phosphate or that consists essentially of calcium and phosphate materials, based on the 3D model provided by the preceding operation 620. Providing may include manufacturing the ceramic scaffold, or obtaining the ceramic scaffold from a manufacturer or supplier. A slurry-based stereolithography 3D printing method as described by Dr. Song Chen (see reference herein above) may be used to manufacture the ceramic scaffold. The manufacturing may include mixing a powdered calcium-phosphate ceramic or pre-ceramic material with a photopolymer resin to create a slurry as feedstock for a stereolithographic additive manufacturing process (e.g., using tape casting as described above), thereby forming a "green" prefired scaffold. The green scaffold, which may include a mixture of ceramic and organic resin and/or a pre-ceramic polymer, may be heated under suitable conditions (e.g., oxidizing or non-oxidizing, depending on the process used) to purge non-ceramic materials and/or transform a pre-ceramic material into a ceramic material, at 630, forming the ceramic scaffold 500 made of a calcium phosphate material, alone or in combination with other materials. Likewise, the method may include manufacturing the scaffold using a 3D printing technique as described herein above, or other suitable method. 3D printing may be especially advantageous for forming the ceramic-resin scaffold when it is desired to custom shape the ceramic-resin scaffold to match an individual morphology of the bone in healthy areas surrounding the defect. For example, the ceramic-resin scaffold may be formed to have an inner surface 520 matching an outer surface of the healthy bone areas. Forming the ceramic-resin scaffold 500 may also include forming a plurality of holes 510 having diameters in the range of about 300μ to 1000μ (e.g., in the range of 500μ to 700μ, or about 700μ) in the ceramic-resin scaffold, for example during the 3D printing process.

The method 600 may further include, at 640, loading the ceramic scaffold with live growth factor transduced cells incorporating a gene that encodes a growth factor essential for bone formation. As discussed above, loading may be performed in vitro, in vivo, or both. In another aspect, the growth factor transduced cells may be prepared for incorporating the gene that encodes the growth factor by transducing the gene into the growth factor transduced cells. For example, the method may include preparing the growth factor transduced cells incorporating the gene that encodes the growth factor by a lentiviral based transcriptional activation system expressing bone morphogenetic protein 2.

Having thus described embodiments of methods and apparatus for repairing a bone defect or providing a ceramic scaffold loaded with growth factor transduced cells, it should also be appreciated that various modifications, adaptations, and alternative embodiments thereof may be made within the scope and spirit of the present invention. For example, 3D printed calcium ceramic scaffolds have been disclosed, but the inventive concepts described above may be equally applicable to scaffolds of other ceramic materials, or scaffolds made by other manufacturing methods than disclosed herein above. In addition, a culture of growth factor transduced cells incorporating a gene that encodes a growth factor essential for bone formation may be prepared by any suitable method whether or not described herein.

The invention claimed is:

1. A method for repairing a bone defect of a patient, comprising:
characterizing a bone defect;
   providing a 3D model of a scaffold for bridging the bone defect;
   providing a 3D ceramic scaffold comprising calcium and phosphate based on the 3D model,
   wherein the 3D ceramic scaffold comprises a tube-like structure, comprising an inner surface and an exterior surface,
   wherein the inner surface matches an outer surface of healthy bone that surrounds the bone defect;
   placing the 3D ceramic scaffold into the bone defect of the patient such that the 3D ceramic scaffold spans the bone defect;
   incorporating a lentiviral based transcriptional activation system expressing bone morphogenetic protein 2 (BMP-2) into cells; and
   culturing in vitro the cells containing the lentiviral based transcriptional activation system on the exterior surface of the 3D ceramic scaffold, thereby forming an assembly that comprises the 3D ceramic scaffold and the cells containing BMP-2,
   wherein placing the 3D ceramic scaffold into the bone defect of the patient is performed before incorporating the lentiviral based transcriptional activation system expressing bone morphogenetic protein 2 (BMP-2) into cells.

2. The method of claim 1, further comprising forming the ceramic scaffold by 3D printing a calcium phosphate material.

3. The method of claim 2, wherein forming the ceramic scaffold further comprises preparing a slurry including a calcium phosphate powder and a resin, forming a ceramic-resin scaffold by 3D-printing the slurry, and removing the resin from the ceramic-resin scaffold by heating.

4. The method of claim 1, wherein providing the 3D model comprises shaping 3D model for causing the ceramic scaffold to match undamaged areas adjacent to the bone defect, so as to fit against the undamaged areas while spanning the bone defect.

5. The method of claim 1, wherein providing the 3D ceramic scaffold comprises forming a plurality of holes in the range of 300 microns to 1000 microns in the ceramic scaffold.

6. The method of claim 1, wherein the cells are selected from mesenchymal cells or bone marrow cells.

* * * * *